US008155978B2

(12) United States Patent
Assmann et al.

(10) Patent No.: US 8,155,978 B2
(45) Date of Patent: Apr. 10, 2012

(54) OPERATING METHOD FOR A COMPUTER

(75) Inventors: Stefan Assmann, Erlangen (DE); Klaus Hambüchen, Hemhofen (DE); Joachim Hornegger, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1264 days.

(21) Appl. No.: 10/851,934

(22) Filed: May 21, 2004

(65) Prior Publication Data
US 2004/0243442 A1 Dec. 2, 2004

(30) Foreign Application Priority Data

May 23, 2003 (DE) .................................. 103 23 822

(51) Int. Cl.
*G06Q 10/00* (2012.01)
(52) U.S. Cl. ............ 705/2; 600/425; 600/300; 600/407; 348/65
(58) Field of Classification Search ................... 705/2, 3; 1/1; 345/764; 600/300, 407, 425; 348/65
See application file for complete search history.

(56) References Cited

U.S. PATENT DOCUMENTS

| | | | |
|---|---|---|---|
| 5,269,301 A * | 12/1993 | Cohen | 607/6 |
| 6,241,668 B1 | 6/2001 | Herzog | |
| 6,353,445 B1 * | 3/2002 | Babula et al. | 715/733 |
| 6,574,629 B1 * | 6/2003 | Cooke et al. | 1/1 |
| 6,611,846 B1 * | 8/2003 | Stoodley | 707/104.1 |
| 6,614,453 B1 * | 9/2003 | Suri et al. | 715/764 |
| 7,457,656 B2 * | 11/2008 | Judd et al. | 600/407 |
| 2003/0046111 A1 * | 3/2003 | Snitkin | 705/2 |
| 2004/0088193 A1 * | 5/2004 | Moriyama et al. | 705/3 |
| 2004/0230458 A1 * | 11/2004 | Takayama et al. | 705/3 |
| 2005/0065813 A1 * | 3/2005 | Mishelevich et al. | 705/2 |

FOREIGN PATENT DOCUMENTS

DE 198 02 572 A1 8/1999
* cited by examiner

*Primary Examiner* — Valerie Lubin
(74) *Attorney, Agent, or Firm* — Schiff Hardin LLP

(57) ABSTRACT

A user predefines for a computer a retrieval instruction for primary data of a patient or of several patients. The computer accesses the primary data of this patient and outputs them to the user via a visual display device. The primary data comprise the primary image data recorded by way of a primary imaging modality and/or primary information derived from said primary image data. The computer automatically checks whether it is possible to access secondary data of this patient, which comprise the secondary image data recorded via a secondary imaging modality and/or secondary information derived from said secondary image data. In the affirmative case, the computer outputs a corresponding message to the user via the visual display device and/or by accessing at least a portion of the secondary data of this patient and outputting said data to the user via the visual display device.

7 Claims, 5 Drawing Sheets

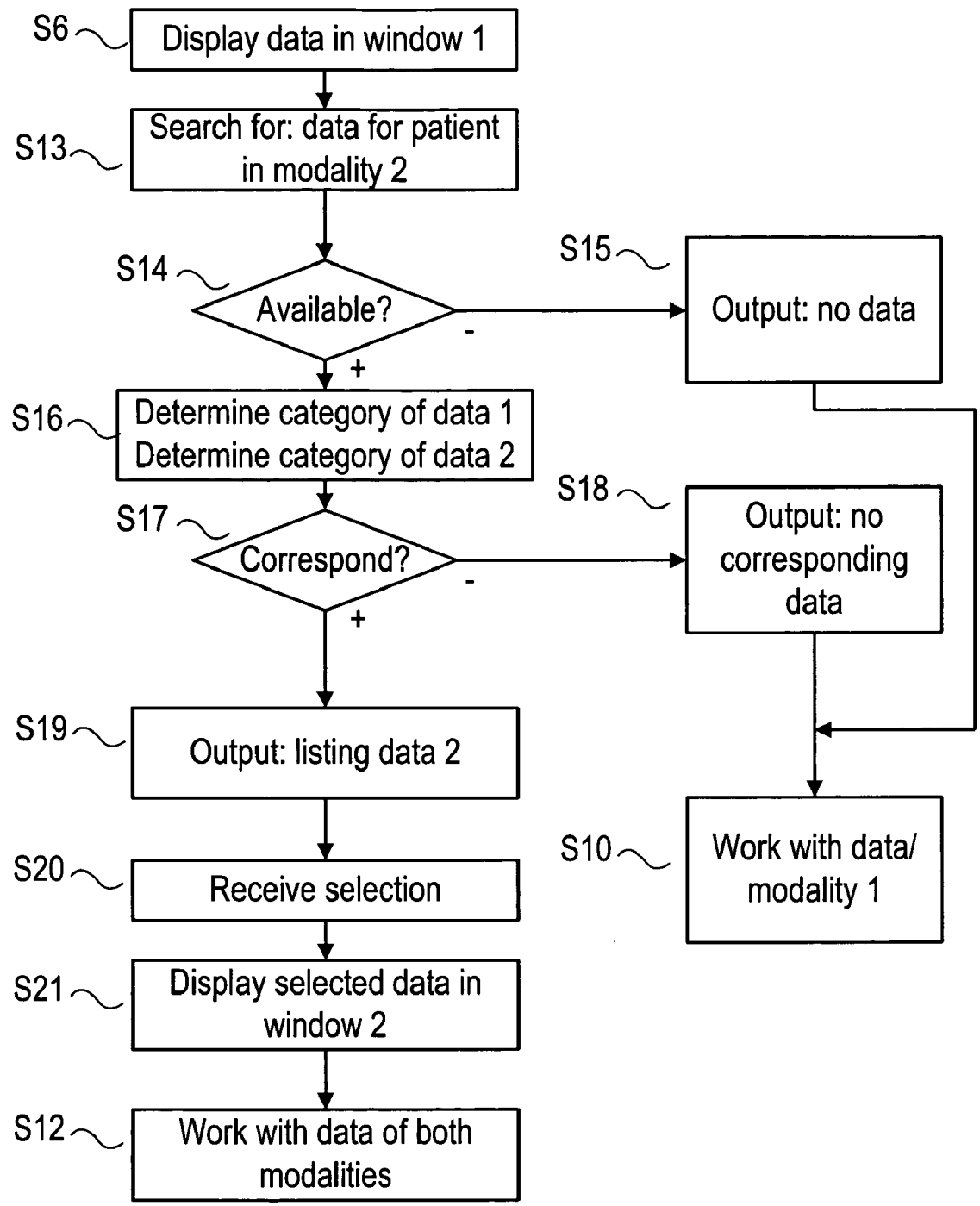

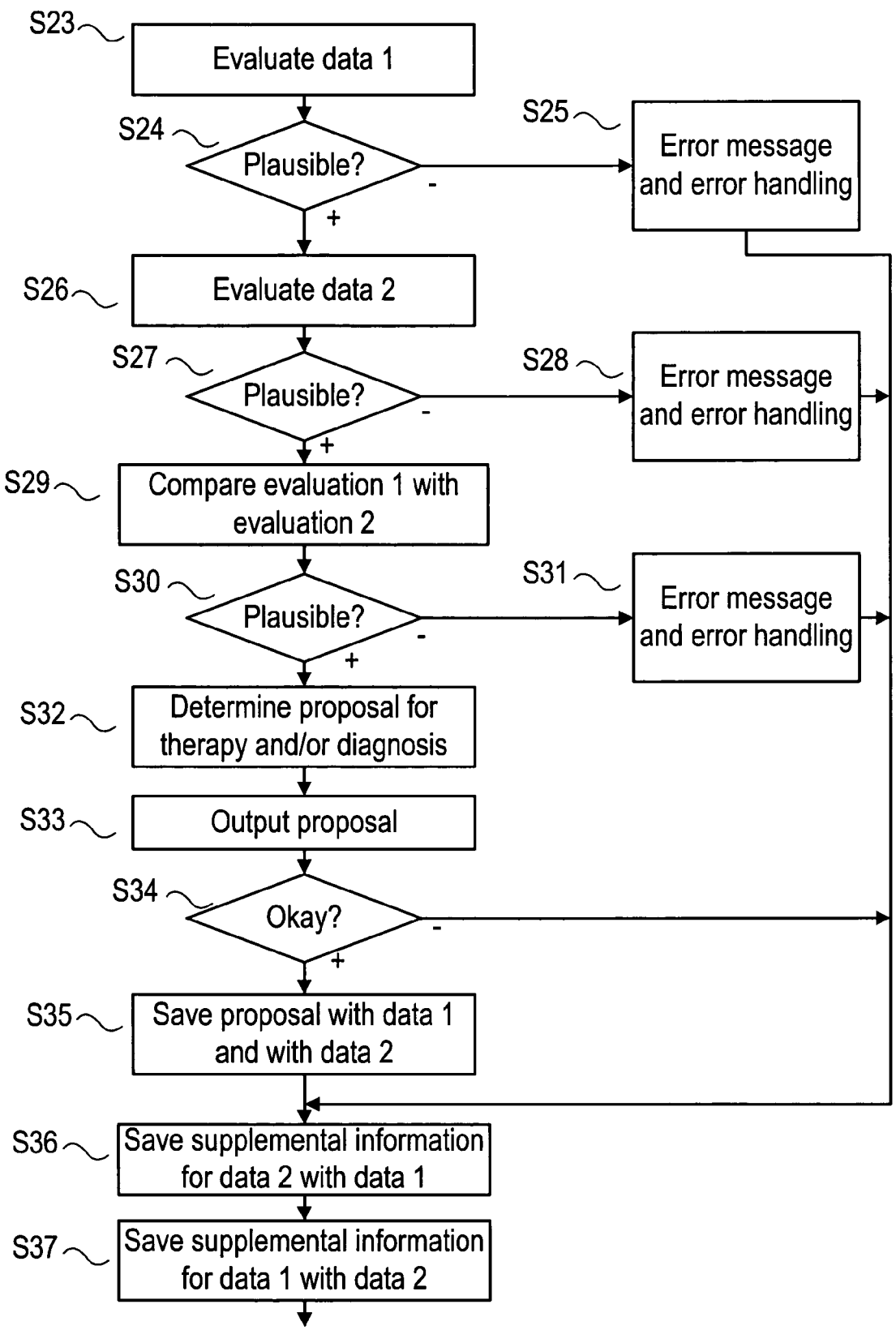

OPERATING METHOD FOR A COMPUTER

BACKGROUND OF THE INVENTION

The present invention relates to an operating method for a computer in which: 1) primary data of patients are accessible from the computer, 2) the primary data comprise primary image data recorded by way of a primary imaging modality and/or primary information derived from the primary image data, 3) the computer receives a retrieval instruction from a user for primary data of one of the patients, 4) secondary data of patients are also accessible from the computer, 5) the secondary data comprise the secondary image data recorded by way of a secondary imaging modality and/or secondary information derived from the secondary image data, and 5) the computer accesses the primary data of this patient and outputs this data to the user via a visual display device.

Such operating methods are known; they are used, among other things, in the evaluation of magnetic resonance or angiography photographs. German patent document DE 198 02 572 A1 discloses an exemplary system.

For example, a physician evaluates angiographic photographs of coronary arteries in order to be able to make inferences about possible stenoses. Physicians also evaluate magnetic resonance images of the heart in order to be able to detect a potential heart attack, its location, and its strength.

SUMMARY OF THE INVENTION

The present invention provides an operating method for a computer by way of which it is possible to get a correlated display playback of the primary and secondary data in simple fashion.

The task is solved by a method that has a computer automatically check upon the retrieval of the primary data as to whether it can access the secondary data of this patient, and, in the affirmative case, has the computer output a corresponding message to the user via the visual display device and/or by accessing at least a portion of the secondary data of this patient and outputting this data to the user via the visual display device.

Thus with the retrieval of the primary data of a patient, the user automatically also receives the secondary data of this patient or at least a message as to the availability of said secondary data.

Various embodiments of the invention are discussed below. If the primary and secondary data are categorized, it is even possible to have the computer use the category of the primary data of this patient to determine the correlated secondary data of the patient and have the computer output to the user the message and/or the part of the secondary data of the patient only in the case of a determination of correlated secondary data of the patient via the visual display device.

If only a message occurs, this message preferably comprises a listing of the existing or correlated secondary data of this patient. In this case it is possible that the user will predefine for the computer a selection instruction for a part of the existing or correlated secondary data of this patient and that the computer then accesses the secondary data of this patient specified by way of the selection instruction and outputs the secondary data to the user via the visual display device If the computer automatically evaluates the primary and/or secondary data of this patient and outputs to the user a proposal for therapy or diagnosis via the visual display device, the flow of the operating method for the user turns out to be particularly comfortable. However, the acceptance of the proposal for therapy or diagnosis by the computer preferably does not take place until after the input of a confirmation instruction. Preferably the computer thus prompts the user for a confirmation instruction and if necessary saves the proposal for therapy or diagnosis allocating it to the primary and/or secondary data of this patient.

If the computer assigns supplementary information to the primary and/or secondary data of this patient, which with regard to this patient is accessible to secondary or primary data, this information will be immediately available in the case of a subsequent, renewed access to the primary and/or secondary data. The supplementary information can in the process comprise in particular contextual information about the secondary or primary data of this patient and about options for accessing this data.

If the computer checks the primary and/or secondary data of this patient for plausibility and outputs the results of its check to the user via the visual display device, dangerous misdiagnoses can be prevented. In particular, via such plausibility checks, it is possible, for example, to determine that the secondary data are contradictory to the primary data.

DESCRIPTION OF THE DRAWINGS

Further advantages and details result from the following description of an embodiment in connection with the drawings.

FIG. 6-8 are flow charts illustrating various aspects according to the method.

DETAILED DESCRIPTION OF THE PREFERRED EMBODIMENTS

Figure 1:
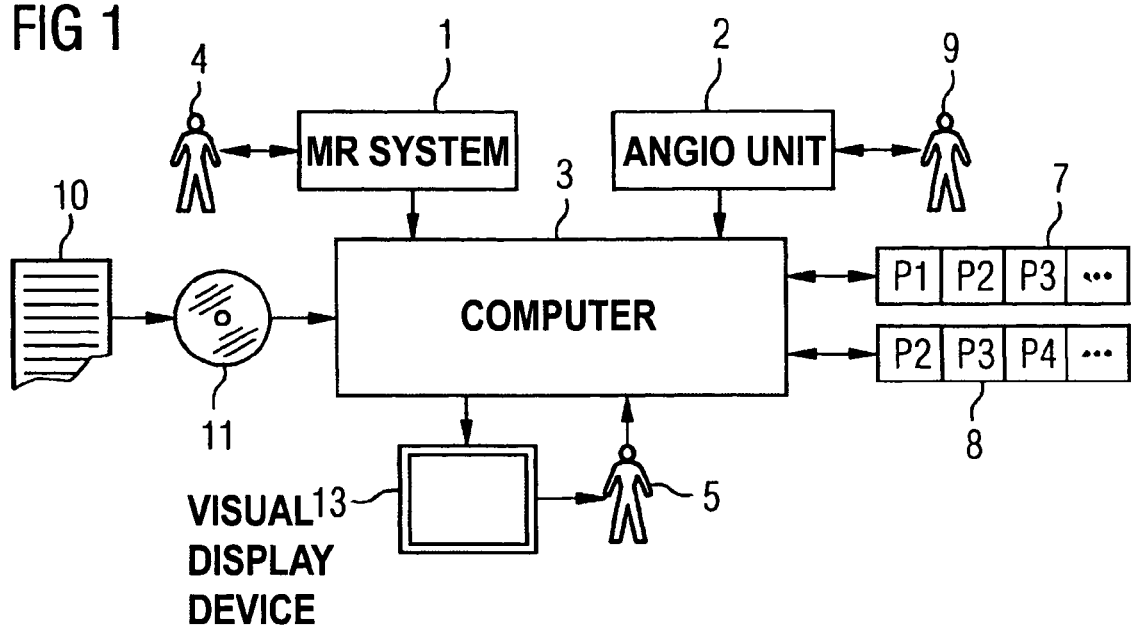
FIG. 1 is a block diagram showing an arrangement of medical devices.

FIG. 1 displays a system used to illustrate an embodiment of the invention having an arrangement of medical devices that exhibits a primary imaging modality 1, a secondary imaging modality 2 and a computer 3. The primary imaging modality 1 can, for example, be designed as a magnetic resonance system or as a computer tomograph. The secondary imaging modality 2 can, for example, be designed as an angiography-x-ray unit or as an ultrasonograph.

The primary imaging modality 1 is operated by a primary modality operator 4. In the operation of the first imaging modality 1, photographs (images), among other things, of patients P1, P2 are created. The first imaging modality 1 automatically also feeds photographs, a photograph time, a photograph category as well as a patient identification to the computer 3. The photograph category specifies, e.g., which body part of patient P1, has been photographed and/or the purpose for which the photographs were created. The photograph category could, for example, specify "Heart" and "Checking for heart attack".

The computer 3 processes the photographs. In particular, the computer 3 can, for example, use the supplied photographs to determine a volume data record which supplies comprehensive information about the affected patient P1, and which therefore can be better evaluated by a user 5 of the computer 3. If necessary, the computer 3 can also perform an automatic evaluation (diagnosis) of the transmitted data. As an alternative, the user 5 can predefine the evaluation for the computer 3.

Figure 2:
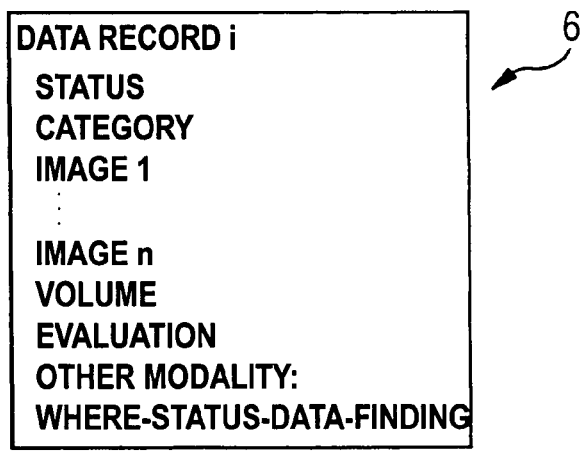
FIG. 2 is an exemplary data record diagram.

FIG. 2 shows an exemplary data record 6 created or supplemented by the computer 3. First of all, the data record 6 contains a status, i.e., the photograph time, as well as the category of the data record 6. It further contains the photographs (images) as such and/or any determined volume data record. Finally, the data record 6 contains the evaluation results. Both the volume date record and the evaluation results are made up of information that has been derived from the image data.

Figure 3:
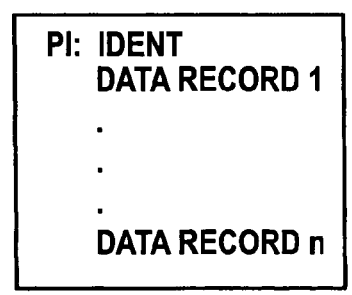
FIG. 3 is an exemplary record diagram showing patient data.

The computer 3 places the thus determined data record 6 in a primary modality data memory. This placement takes place as per FIG. 3 under allocation to the relevant patient P1-Pn.

Not only is it possible to access the primary modality data memory 7 from the computer 3, but rather it is also possible to access a secondary modality data memory 8. The secondary modality data memory 8 contains those patient data that are fed to the computer 3 on the basis of corresponding defaults by a second modality operator 9 of the secondary imaging modality 2. The collaboration of the secondary imaging modality 2 with the computer 3 takes place in the same manner as the collaboration of the primary imaging modality 1 with the computer 3. However, the categories of the photographs can deviate from those of the primary imaging modality 1. For example, in the case of angiographic photographs, the term "coronary arteries" can be specified as a photographed body region and as purpose of the photograph "Checking for stenoses" can be specified.

The computer 3 is programmed with a computer program 10, which is fed to the computer 3 using a data storage medium 11, for example a CD-ROM 11. The computer program 10 is stored on the data storage medium 11 in (exclusively) machine-readable format. On the basis of the programming with the computer program 10, the computer 3 executes an operating method described in greater detail below in connection with FIG. 4.

Figure 4:
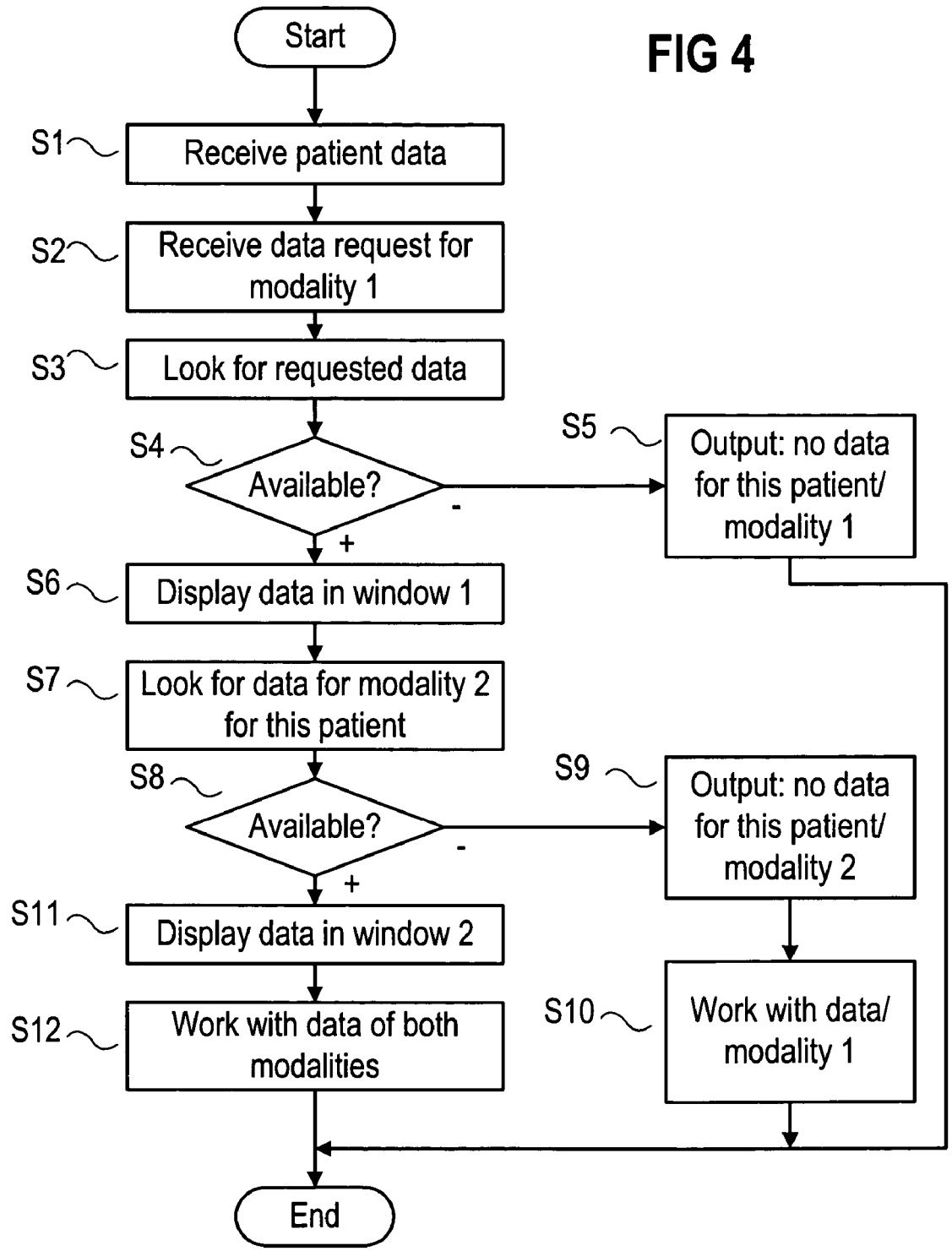
FIG. 4 is a flow chart illustrating an embodiment of the inventive method.

FIG. 4 illustrates the computer 3 receiving patient data in one step S1 and saving the data in one of the modality data memories 7, 8. This receipt of data has been discussed above in connection with FIG. 2 and FIG. 3. Then, in a step S2, the computer 3 receives a data request for a patient's data, e.g., patient P2, via a dialog box 12 of a visual display device 13 (see FIG. 1 and FIG. 5). The data request corresponds to a retrieval instruction for the data of this patient P2 from the first modality data memory 7. The computer 3 then accesses the first modality data memory 7. It determines data or data of the requested category of the relevant patient P2.

In a step S4, the computer 3 then checks whether it has found such data of patient P2. Depending on the outcome of its check, it performs either a step S5 or a step S6.

Figure 5:
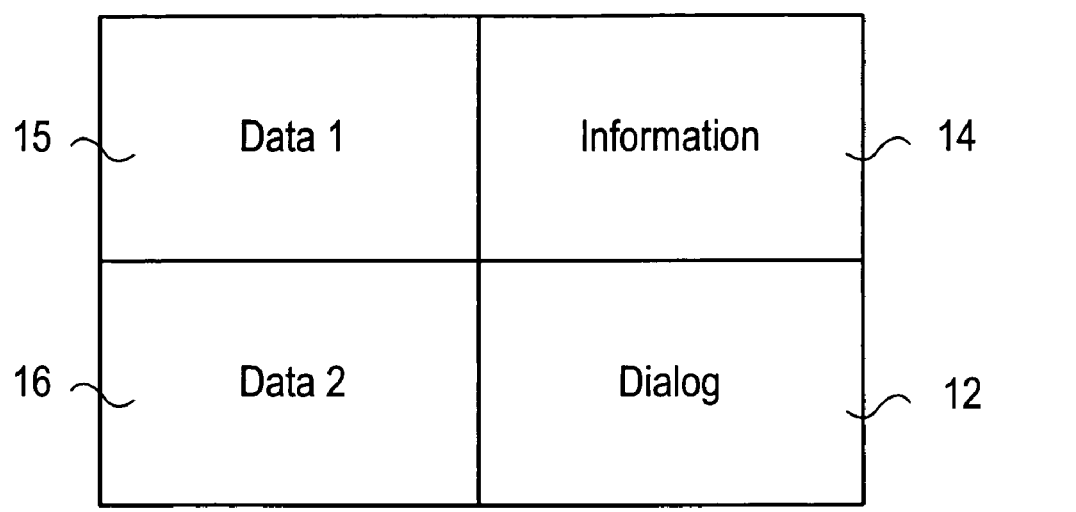
FIG. 5 is a block diagram illustrating a monitor display.

If the computer 3 was not able to verify any data, then in a step S5, it outputs a corresponding message to this effect to the user 5 via an information window 14 (see FIG. 5). If on the other hand the computer 3 was able to locate corresponding data, the computer 3 accesses the data of this patient P2 and outputs the data to the user 5 via a first data window 15 of the visual display device 13.

After step S6, the computer 3 executes a step S7. In step S7, the computer 3 accesses the second modality data memory 8. It checks whether there are any data there for the same patient P2, or, in the case of categorization, whether there are any data of the corresponding category there. For example, if the category of the data of the first imaging modality 1 is "Heart and Checking for heart attack", with regard to the data of the second imaging modality 2, the computer 3 could check for data from the category "Coronary arteries and Checking for stenoses".

In step S8, the computer 3 checks whether it found the data it was searching for. If it did not find any such data, it executes steps S9 and S10. If it did find such data, it executes steps S11 and S12.

In step S9, the computer 3 outputs a message to the user stating that there are no corresponding data available for this patient P2 from the second imaging modality 2. In step S10 the computer 3 then collaborates with the user 5 with regard to the data of the first imaging modality 1 in known fashion.

If the computer 3, on the other hand, found corresponding data of the second imaging modality 2, in step S11 it displays the data or part of the data in a second data window 16 and in this way outputs the data to the user 5. In step S12 it is then possible to work with data of both imaging modalities 1, 2 via dialog box 12 and data windows 15, 16.

The above described embodiment of a basic operating method can be designed in various ways according to various embodiments of the invention. FIG. 6 shows two such designs.

The first design relates to steps S7, S8 and S9. As per FIG. 6, these steps S7, S8 and S9 are each split up into two partial steps, S13 and S16, S14 and S17, as well as S15 and S18.

As per FIG. 6 in step S13, it is first determined whether the second modality data memory 8 contains any data for this patient P2. In step S14, the corresponding check takes place, in step S15, if necessary, the computer 3 outputs a message to the effect that the second modality data memory 8 does not contain any data for this patient P2.

In step S16, the computer 3 determines the category of the data retrieved from the first modality data memory 7 for the specified patient P2 as well as the category of the data available in the second modality data memory 8. In step S17, the computer 3 determines whether the categories correspond to each other. If the categories do not correspond to one another, in step S18, a message is output to the user 5, stating that there are no corresponding data. In particular in this case, steps S11 and S12 are only executed when correlated data of the second imaging modality 2 for this patient P2 are available.

The second design relates to step S11. As per FIG. 6 this step S11 is split up into three partial steps, S19 through S21. In step S19, a message is output, e.g., via information window 14, to the user 5 which comprises a listing of the available data or of the available correlated data of the second imaging modality 2 for this patient P2. In step S20, the computer 3 receives the data of the second imaging modality 2 specified for this patient P2 by way of the selection instruction and outputs them to the user 5 via the second data window 16 of the visual display device 13.

The two designs can be implemented independently from each other. In particular, e.g. the second design of step S11 can be replaced by the design shown in FIG. 7.

Figure 7:
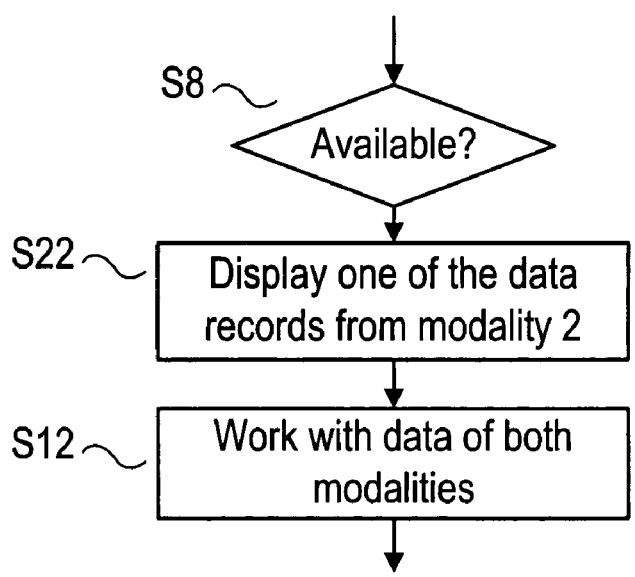

As per FIG. 7, no list is output to the user 5 from which he can then make a selection. Instead, in a step S22 the computer 3 automatically makes its own selection from the available data records 6 and displays the selected data record 6 in the second data window 16. For example, the computer 3 can select and display the data record 6 with the closest categorization, in the case of several data records 6 with the applicable categorization, it can select and display the most recent of these data records 6.

In a simple version of the operating method according to an embodiment of the invention, a pure dialog operation between the computer 3 and the user 5 takes place in step S12. In particular, all changes of existing data take place only on the basis of a direct input of the user 5. In another version, which will be described below in combination with FIG. 8, it is however also possible to have the computer 3 make evaluations and changes in the data.

Thus, as per FIG. 8, it is, for example, possible in a step S23 to have the computer 3 automatically evaluate the data of the patient P2 with regard to the first imaging modality 1 and in a step S24 check for plausibility. If the data are not plausible, in a step S25, the computer 3 outputs an error message to the user 5 and performs error handling.

In similar fashion, in a step S26, for example, the computer 3 evaluates data of the patient P2 that were generated by way of the second imaging modality 2. In a step S27 the computer 3 also checks these data for plausibility. If necessary, in a step S28, the computer 3 outputs an error message to the user 5 and performs error handling.

Above all, however, in a step S29, it is possible to have the computer 3 compare the evaluations performed in S23 and S26 with each other. For example, if infarcted tissue is detected in a specified region of the heart, a corresponding coronary artery should exhibit a stenosis. Thus, in a step S30, the data can be checked for plausibility in both modalities.

If necessary, in a step S31, an error message can again be output to the user 5 and a corresponding error handling can be performed. In this way, for example, it is possible to check whether the data actually come from the same patient P2 and the receipt times are not too far apart from each other.

The automatic evaluation of the data of patient P2 by the two modalities 1, 2 can even go so far that the computer 3 in a step S32 determines a proposal for therapy and/or diagnosis. However, the proposal is not yet assigned to the data. Instead, the computer 3 first outputs the proposal to the user 5 in a step S33. Only after the user 5 in a step S34 inputs a confirmation instruction does the computer 3 assign the proposal for therapy and diagnosis to the data of both imaging modalities 1, 2 in a step S35 and save it in the data record 6 as a supplement to the specific evaluation.

Finally, it is also possible to have the computer, in a step S36,—compare FIG. 2—assign supplementary information to the data of this patient P2, stating that data of the other imaging modality 2, 1 for this patient P2 and stating that it is possible to access said data. The data can, for example, comprise a memory location or a memory address, an update status, brief information about what kind of data these are, as well as a brief finding of these data.

The aforementioned added-feature functions described in connection with FIG. 8, that is, 1) the plausibility checks, 2) the determination of the proposal for therapy and/or diagnosis, and 3) the assignment of supplementary information, can of course be implemented independently of one another. These functions are additionally independent from the concrete design of steps S7, S8, S9 and S11.

Hence, by way of the operating method of these embodiments of the invention, a simple, cross-modality finding is possible through the user 5 (as a rule, a physician).

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or phisical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. An operating method for a computer, comprising the steps of:

storing a plurality of data of patients for the computer and each of the data comprising respective image data previously recorded via a respective imaging modality which is one of the imaging modalities selected from the imaging modality group consisting of magnetic resonance, computer tomograph, angiography, x-ray, and ultrasonigraph, and each of said data also comprising a respective category name for said image data assigned by said respective imaging modality to said respective image data;

providing by the computer respective supplementary information for each of the data, said respective supplementary information comprising a storage location or a storage address for accessing respective data of a respective patient;

receiving by the computer a retrieval instruction from a user to access one of the stored plurality of data for one of the patients;

in a first accessing by the computer said one of the data of said one patient is accessed and said one of the data is output to the user via a visual display device;

without intervention by said user, automatically checking by the computer upon the first accessing of said one of the data of said one patient availability of an additional data of said one patient related to said one data by comparing a first category name of said one data with a different second category name of said additional data to automatically determine if the two different names both relate to a same body region of the one patient without the user defining said same body region and if so then correlating said one data with said additional data of said one patient, and wherein an imaging modality of said additional data is different than an imaging modality of said one data, both of said imaging modalities being selected from said imaging modality group;

providing a message if additional data for said one patient is not available for the same body region, and if the additional data of said one patient for the same body region is available, the computer automatically performing at least one of: (a) outputting a corresponding message to the user via the visual display device, and (b) accessing at least a portion of the additional data of said one patient and outputting said at least a portion of the additional data to the user via the visual display device; and if the additional data of said one patient with the same body region is available, assigning and saving by the computer said supplementary information for the additional data of said one patient with the one data of said one patient, and also assigning and saving said supplementary information for the one data of said one patient with the additional data of said one patient, so that said supplementary information is immediately available in a later new accessing of the one data or the additional data of said one patient after said first accessing.

2. The method according to claim 1 further comprising automatically evaluating by the computer at least one of the one data and the additional data of said one patient and outputting to the user a proposal for therapy or diagnosis via the visual display device.

3. The method according to claim 2 further comprising prompting by the computer the user for a confirmation instruction.

4. The method according to claim 3 further comprising saving the proposal for therapy or diagnosis, and allocating the proposal to at least one of the one data and the additional data of said one patient.

5. The method according to claim 1 further comprising checking by the computer at least one of the one data and the additional data of said one patient for plausibility, and outputting results of the check to the user via the visual display device.

6. The method according to claim 5 wherein said plausibility check checks for a first medical defect in said one data and compares that first medical defect to a second medical defect detected in said additional data to see if they are plausible with respect to one another for said body region of said one patient and are not contradictory.

7. A non-transitory computer readable medium storing computer instructions which when executed by a computer perform the steps of:

storing a plurality of data of patients for the computer and each of the data comprising respective image data previously recorded via a respective imaging modality which is one of the imaging modalities selected from the imaging modality group consisting of magnetic resonance, computer tomograph, angiography, x-ray, and ultrasonigraph, and each of said data also comprising a respective category name for said image data assigned by said respective imaging modality to said respective image data;

providing by the computer respective supplementary information for each of the data, said respective supplementary information comprising a storage location or a storage address for accessing respective data of a respective patient;

receiving by the computer a retrieval instruction from a user to access one of the stored plurality of data for one of the patients;

in a first accessing by the computer said one of the data of said one patient is accessed and said one of the data is output to the user via a visual display device;

without intervention by said user, automatically checking by the computer upon the first accessing of said one of the data of said one patient availability of an additional data of said one patient related to said one data by comparing a first category name of said one data with a different second category name of said additional data to automatically determine if the two different names both relate to a same body region of the one patient without the user defining said same body region and if so then correlating said one data with said additional data of said one patient, and wherein an imaging modality of said additional data is different than an imaging modality of said one data, both of said imaging modalities being selected from said imaging modality group;

providing a message if additional data for said one patient is not available for the same body region, and if the additional data of said one patient for the same body region is available, the computer automatically performing at least one of: (a) outputting a corresponding message to the user via the visual display device, and (b) accessing at least a portion of the additional data of said one patient and outputting said at least a portion of the additional data to the user via the visual display device; and if the additional data of said one patient with the same body region is available, assigning and saving by the computer said supplementary information for the additional data of said one patient with the one data of said one patient, and also assigning and saving said supplementary information for the one data of said one patient with the additional data of said one patient, so that said supplementary information is immediately available in a later new accessing of the one data or the additional data of said one patient after said first accessing.

\* \* \* \* \*